(12) United States Patent
Liao et al.

(10) Patent No.: US 12,243,636 B2
(45) Date of Patent: Mar. 4, 2025

(54) APPARATUS AND METHOD FOR DIAGNOSING A MEDICAL CONDITION FROM A MEDICAL IMAGE

(71) Applicant: Empallo, Inc., Somerville, MA (US)

(72) Inventors: Ruizhi Liao, Somerville, MA (US); Polina Golland, Cambridge, MA (US)

(73) Assignee: Empallo, Inc., Somerville, MA (US)

( * ) Notice: Subject to any disclaimer, the term of this patent is extended or adjusted under 35 U.S.C. 154(b) by 380 days.

(21) Appl. No.: 17/739,238

(22) Filed: May 9, 2022

(65) Prior Publication Data

US 2022/0375576 A1 Nov. 24, 2022

Related U.S. Application Data

(60) Provisional application No. 63/185,611, filed on May 7, 2021.

(51) Int. Cl.
| | | |
|---|---|---|
| *G16H 30/40* | (2018.01) | |
| *G16H 15/00* | (2018.01) | |
| *G16H 50/20* | (2018.01) | |
| *G16H 50/70* | (2018.01) | |

(52) U.S. Cl.
CPC .............. *G16H 30/40* (2018.01); *G16H 15/00* (2018.01); *G16H 50/20* (2018.01); *G16H 50/70* (2018.01)

(58) Field of Classification Search
CPC ........ G16H 30/40; G16H 15/00; G16H 50/70; G16H 50/20
USPC ........................................................ 382/128
See application file for complete search history.

(56) References Cited

U.S. PATENT DOCUMENTS

| | | | | |
|---|---|---|---|---|
| 10,943,692 | B1* | 3/2021 | Lynn | A61B 5/0022 |
| 11,587,228 | B2* | 2/2023 | Bar | G16H 15/00 |
| 11,763,952 | B2* | 9/2023 | Haghighi | G16H 30/20 |
| 2014/0324469 | A1* | 10/2014 | Reiner | G16H 50/70 |
| | | | | 705/3 |
| 2019/0259492 | A1* | 8/2019 | Reicher | G06T 7/0014 |
| 2021/0220470 | A1* | 7/2021 | Bryce | C07K 16/2866 |
| 2021/0326653 | A1* | 10/2021 | Zhou | G06F 18/2155 |
| 2021/0342646 | A1* | 11/2021 | Feng | G06T 7/11 |
| 2021/0343014 | A1* | 11/2021 | Haghighi | G06V 10/25 |

(Continued)

OTHER PUBLICATIONS

Zhang, TandemNet: Distilling Knowledge from Medical Images Using Diagnostic Reports as Optional Semantic References, arXiv (Year: 2017).*

*Primary Examiner* — William D Titcomb
(74) *Attorney, Agent, or Firm* — Caldwell Intellectual Property Law

(57) ABSTRACT

An apparatus for diagnosing a medical condition including at least a processor and a memory, the memory containing instructions configuring the at least a processor to receive a medical image that is the result of a medical imaging procedure and train a medical image classifier and a medical report classifier. Training the classifiers includes receiving training data, including a plurality of prior medical images and a plurality of prior medical reports, training the medical image classifier and the medical report classifier, and optimizing both classifiers using a common loss function. The memory further containing instructions configuring the at least a processor to generate a label for the medical image, including inputting the medical image into the medical image classifier and receiving the label as output from the medical image classifier.

20 Claims, 9 Drawing Sheets

(56) References Cited

U.S. PATENT DOCUMENTS

| | | | |
|---|---|---|---|
| 2022/0309811 A1* | 9/2022 | Haghighi | G06V 10/764 |
| 2022/0328189 A1* | 10/2022 | Zhou | G06V 10/82 |
| 2022/0375576 A1* | 11/2022 | Liao | G16H 30/40 |
| 2024/0105336 A1* | 3/2024 | Liao | G16B 20/00 |

* cited by examiner

APPARATUS AND METHOD FOR DIAGNOSING A MEDICAL CONDITION FROM A MEDICAL IMAGE

CROSS-REFERENCE TO RELATED APPLICATIONS

This application claims the benefit of priority of U.S. Provisional Patent Application Ser. No. 63/185,611, filed on May 7, 2021, and titled "NOVEL ALGORITHMS FOR ASSESSING LUNG PATHOLOGIES INCLUDING FLUID OVERLOAD IN THE LUNGS," which is incorporated by reference herein in its entirety.

FIELD OF THE INVENTION

The present invention generally relates to the field of the diagnosis of medical conditions. In particular, the present invention is directed to an apparatus and method for diagnosing a medical condition from a medical image.

BACKGROUND

Medical imaging procedures are common ways to diagnose medical conditions. However, they need a skilled practitioner in order to be able to read and correctly interpret the resulting medical images. These practitioners can be expensive, busy, or in short supply. Existing solutions do not adequately resolve this problem.

SUMMARY OF THE DISCLOSURE

In an aspect, a method for diagnosing a medical condition, the method including receiving a medical image, wherein the medical image is the result of a medical imaging procedure. The method further including training a medical image classifier and a medical report classifier, wherein training the medical image classifier and the medical report classifier includes receiving training data, wherein the training data comprises a plurality of prior medical images and a plurality of prior medical reports, wherein each prior medical image of the plurality of prior medical images is associated with a prior medical report of the plurality of prior medical reports to form an image-text pair, training the medical image classifier and the medical report classifier using the training data. and optimizing both of the image classifier and the medical report classifier using a common loss function. The method further including generating a label for the medical image, wherein generating the label for the medical image includes inputting the medical image into the medical image classifier and receiving the label as output from the medical image classifier.

In another aspect, an apparatus for diagnosing a medical condition, the apparatus including at least a processor and a memory communicatively connected to the processor, the memory containing instructions configuring the at least a processor to receive a medical image, wherein the medical image is the result of a medical imaging procedure and train a medical image classifier and a medical report classifier. Training the medical image classifier and the medical report classifier includes receiving training data, wherein the training data comprises a plurality of prior medical images and a plurality of prior medical reports, wherein each prior medical image of the plurality of prior medical images is associated with a prior medical report of the plurality of prior medical reports to form an image-text pair, training the medical image classifier and the medical report classifier using the training data, and optimizing both of the image classifier and the medical report classifier using a common loss function. The memory further containing instructions configuring the at least a processor to generate a label for the medical image, wherein generating the label for the medical image includes inputting the medical image into the medical image classifier and receiving the label as output from the medical image classifier.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for diagnosing a medical condition. In an embodiment, a medical image classifier may be used to generate a label for a medical image. The label may denote the severity of a medical condition indicated by the medical image. The label may be part of a classifier report, containing further information such as explanations, a diagnosis, treatment timelines, and the like.

Aspects of the present disclosure can be used to train a medical image classifier and a medical report classifier. Use a joint loss function in order to optimize both of the medical image classifier and the medical report classifier. Aspects of the present disclosure also allow for the medical image classifier to be decoupled from the medical report classifier.

Aspects of the present disclosure allow for a medical image classifier to output a severity label for pulmonary edema. For example, medical image classifier may do this when it is given a chest radiograph.

Figure 1:
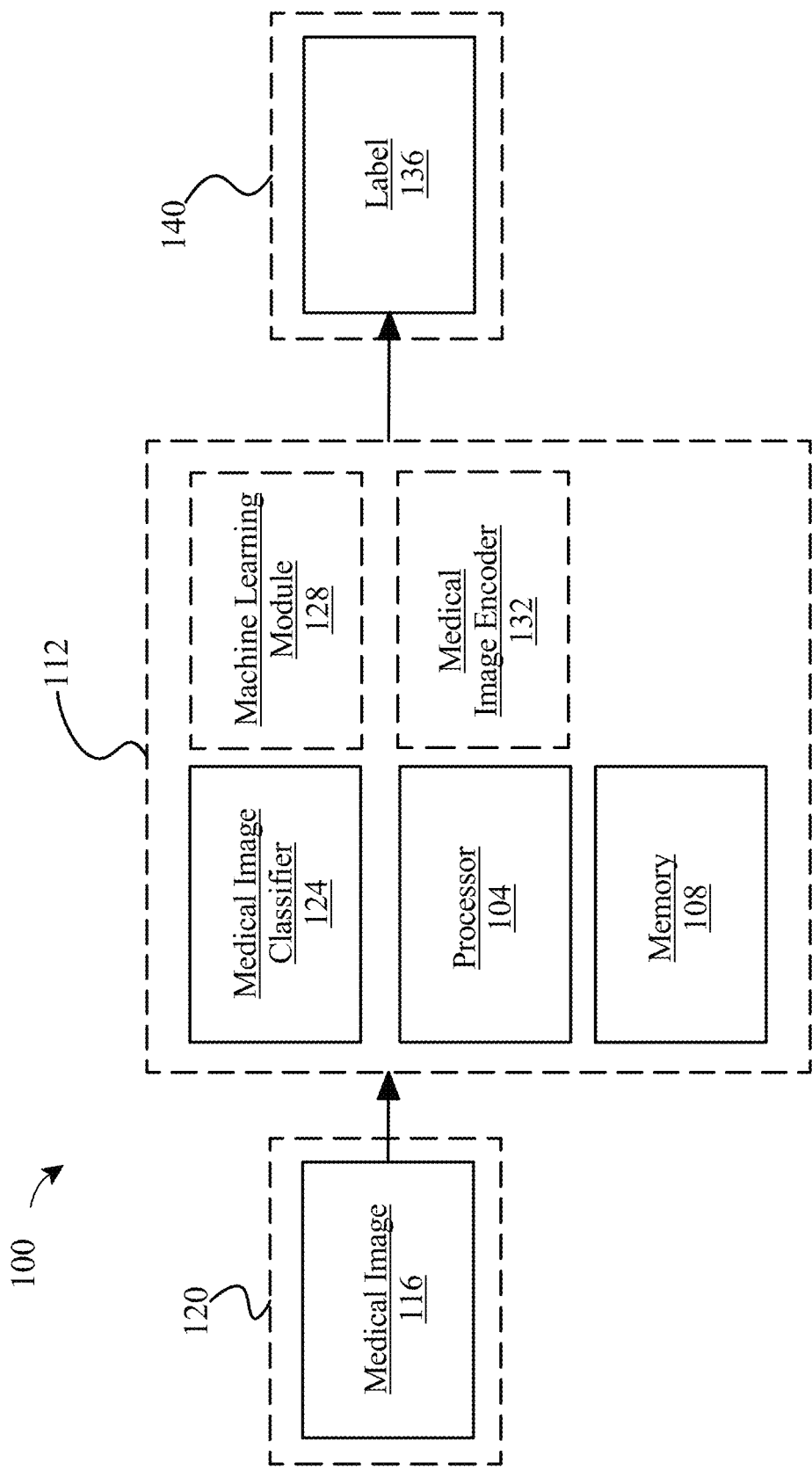
FIG. 1 is a box diagram of an exemplary embodiment of an apparatus for diagnosing a medical condition.

Referring now to FIG. 1, an exemplary embodiment of an apparatus for diagnosing a medical condition 100 is illustrated. Apparatus 100 includes a processor 104 and memory 108 communicatively connected to processor 104, memory 108 containing instructions for processor 104 to execute. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure. In some embodiments, medical image database 120 may be connected to computing device 112 by a wireless connection, such as a cellular connection, 3G, 4G, LTE, 5G, Bluetooth, WiFi, radio, and the like.

With continued reference to FIG. 1, apparatus 100 may include computing device 112, wherein the computing device 112 may include processor 104 and memory 108. Computing device 112 may include any computing device 112 as described in this disclosure, including without limitation a microcontroller, microprocessor, digital signal processor (DSP) and/or system on a chip (SoC) as described in this disclosure. Computing device 112 may include, be included in, and/or communicate with a mobile device such as a mobile telephone or smartphone. Computing device 112 may include a single computing device 112 operating independently, or may include two or more computing device 112 operating in concert, in parallel, sequentially or the like; two or more computing devices may be included together in a single computing device 112 or in two or more computing devices. Computing device 112 may interface or communicate with one or more additional devices as described below in further detail via a network interface device. Network interface device may be utilized for connecting computing device 112 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 112 may include but is not limited to, for example, a computing device 112 or cluster of computing devices in a first location and a second computing device 112 or cluster of computing devices in a second location. Computing device 112 may include one or more computing devices dedicated to data storage, security, distribution of traffic for load balancing, and the like. Computing device 112 may distribute one or more computing tasks as described below across a plurality of computing devices of computing device, which may operate in parallel, in series, redundantly, or in any other manner used for distribution of tasks or memory between computing devices. Computing device 112 may be implemented using a "shared nothing" architecture in which data is cached at the worker, in an embodiment, this may enable scalability of system 100 and/or computing device.

With continued reference to FIG. 1, computing device 112 may be designed and/or configured to perform any method, method step, or sequence of method steps in any embodiment described in this disclosure, in any order and with any degree of repetition. For instance, computing device 112 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 112 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, processor 104 is configured to receive a medical image 116. For the purposes of this disclosure, a "medical image," is the result of a medical imaging procedure. A "medical imaging procedure," for the purposes of this disclosure, is a process of imaging the interior of a body for medical purposes. As a non-limiting example, a medical imaging procedure may include radiography. "Radiography," for the purposes of this disclosure refers to the technique of using radiation to view of the internal form of an object. Radiography may include projectional radiography, where objects are exposed to high-energy forms of radiation (such as X-rays) and the resulting remnant beam is captured as a latent image. Radiography may include computed tomography, wherein ionizing radiation is used in conjunction with a computer. Computed tomography may be referred to as a "CT scan" or "CAT scan." Radiography may include dual energy X-ray absorptiometry, wherein X-rays are emitted in two narrow beams that are 90 degrees apart and used to scan across the patient. Dual energy X-ray absorptiometry may be referred to as "DEXA" or "bone densitometry." Additionally, dual energy X-ray absorptiometry may be used, as a non-limiting example, for osteoporosis tests. Radiography may include fluoroscopy. Fluoroscopy is a technique used to create moving projection radiographs. Fluoroscopy may be sued to track a tissue or contrast agent in order to, as a non-limiting example, guide a medical intervention. A biplanar fluoroscopy may display two planes at the same time, as opposed to a single plane fluoroscopy which only displays one plane. Radiography may include angiography. Angiography includes the use of fluoroscopy to view the cardiovascular system. As a non-limiting example, during an angiography an iodine-based contrast medium may be injected into a patient's bloodstream and tracked. Radiography may include contrast radiography. Contrast radiography includes the use of a radiocontrast agent in order to make structures of interest stand out such that they can be examined.

With continued reference to FIG. 1, a medical imaging procedure may include magnetic resonance imaging (MRI). MRIs use strong magnetic fields, magnetic field gradients, and radio waves to form images of the anatomy and processes of the body. Magnetic resonance imaging may include magnetic resonance neuroimaging, magnetic resonance imaging of the brain, cardiac magnetic resonance imaging, functional magnetic resonance imaging, spinal functional magnetic resonance imaging, hepatobiliary magnetic resonance, magnetic resonance angiography, and the like.

With continued reference to FIG. 1, a medical imaging procedure may include nuclear medicine imaging. Nuclear medicine imaging involves measuring radiation emitting from within the body of a patient. Thus, it can be distinguished from radiology where external sources of radiation are used. As part of nuclear medicine imaging, radiopharmaceuticals may be taken by the patient (as non-limiting examples, through inhalation, intravenously, or orally). External detectors may then be used to capture images using the radiation emitted by the radiopharmaceuticals. The external detectors may, as a non-limiting example, include gamma cameras. Nuclear medicine imaging may include hybrid techniques from modalities such as CTs or MRIs.

With continued reference to FIG. 1, a medical imaging procedure may include ultrasound. An ultrasound used high frequency broadband sound waves that may be reflected by tissue in order to produce images. These images may be 2D or 3D. As a non-limiting example, an ultrasound may be used to image the fetus of a pregnant woman. As further non-limiting examples, ultrasound may be used to image the abdominal organs, heart, breast, muscles, tendons, arteries, and/or veins. A medical imaging procedure may include echocardiography. Echocardiography refers to using ultrasound imaging to image the heart of a patient. A person of ordinary skill in the art, after having reviewed the entirety of this disclosure, would appreciate that a variety of medical imaging procedures may be used.

With continued reference to FIG. 1, medical image 116 may include images, photographs, visual representations, and the like, created by any of the aforementioned medical imaging procedures. As a non-limiting example, angiography may produce an angiograph. As another non-limiting example, radiography may produce a radiograph. A person of ordinary skill in the art, after having reviewed the entirety of this disclosure, would appreciate that a variety of medical images 116 may be produced depending on the medical imaging procedure used.

With continued reference to FIG. 1, in some embodiments, medical image 116 may include a chest radiograph. A "chest radiograph," for the purposes of this disclosure, is a projection radiograph of the chest of a subject. In some cases, a chest radiograph may be referred to as a "chest X-ray," "CXR," or "chest film." Chest radiographs may be used to assess and/or diagnose conditions effecting the chest, its contents, and nearby structures. Chest radiographs may be used to assess or diagnose pulmonary edema. For the purposes of this disclosure, "pulmonary edema" is a condition caused by excess fluid in the lungs. As a non-limiting example, fluid may collect within the air sacs of the lungs. Pulmonary edema may indicate heart problems. For example, pulmonary edema may be common in patients seeking treatment for acute congestive heart failure (CHF). In addition to being used to detecting the presence or absence of pulmonary edema, chest radiographs may be used to quantify pulmonary edema (as a non-limiting example, quantifying the severity of the pulmonary edema.) This may be useful in order to manage patient fluid status, for example for a patient suffering from CHF. Treatment success in acute CHF cases depends crucially on effective management of patient fluid status; thus, quantification of pulmonary edema may be useful for this.

With continued reference to FIG. 1, medical image 116 may be received from a medical image database 120. Medical image database 120 may be implemented, without limitation, as a relational database, a key-value retrieval database such as a NOSQL database, or any other format or structure for use as a database that a person skilled in the art would recognize as suitable upon review of the entirety of this disclosure. Medical image database 120 may alternatively or additionally be implemented using a distributed data storage protocol and/or data structure, such as a distributed hash table or the like. Medical image database 120 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure. Computing device 112 may be communicatively connected to medical image database 120.

With continued reference to FIG. 1, in some embodiments, computing device 112 may receive a medical image 116 by way of a user's selection. As a non-limiting example, user may choose a medical image 116 for computing device 112 to use. This may be done, as non-limiting example, by locating the medical image 116 on a storage device or uploading medical image 116 to the cloud. A person of ordinary skill in the art, after having reviewed the entirety of this disclosure, would appreciate that computing device 112 may receive medical image 116 in a variety of ways.

With continued reference to FIG. 1, computing device 112 includes a medical image classifier 124. Processor 104 trains a medical image classifier 124. Processor 104 may use machine learning module 128 to train medical image classifier 124. Machine learning module 128 may be consistent with machine learning module 700 disclosed with reference to FIG. 7. Medical image classifier 124 may be trained using the medical image classifier and medical report classifier training system 200 disclosed with reference to FIG. 2.

With continued reference to FIG. 1, computing device 112 may include an medical image encoder 132. An "image encoder," for the purposes of this disclosure, is an element that converts images into image feature representations. An "image feature," for the purposes of this disclosure is an individually measurable property or characteristic of an image. In some embodiments, medical image encoder 132 may be an autoencoder. In some embodiments, medical image encoder 132 may be a variational autoencoder. A "autoencoder," for the purposes of this disclosure, is an artificial neural network architecture used to learn efficient codings of unlabeled data. For a variational autoencoder the encodings distribution of the autoencoder may be regularized during training. Medical image encoder 132 may be trained to reconstruct images from the image feature representations. In some embodiments, medical image encoder 132 may include an encoder and a decoder. In some embodiments, the variational auto encoder may include an encoder and a decoder. In some embodiments, the encoder of may have residual blocks. In some embodiments, the encoder may have eight residual blocks. In some embodiments, the decoder may have deconvolution layers. In some embodiments, the decoder may have five deconvolution layers. In some embodiments, medical image encoder 132 may include transposed convolutional layers. In some embodiments, a neural network, disclosed with reference to FIG. 5 and FIG. 6 may be used to implement medical image encoder 132.

With continued reference to FIG. 1, processor 104 generates a label 136 for the medical image 116. Generating label 136 includes inputting medical image 116 into medical image classifier. Generating label 136 also includes receiving label 136 as output from medical image classifier 124. For the purposes of this disclosure, a "label" is information concerning a medical image that is received as output from a medical image classifier. In some embodiments, label 136 may comprise a severity of a medical condition. As a non-limiting example, wherein the medical image 116 is a chest radiograph, label 136 may denote the severity of a pulmonary edema. In some embodiments, label 136 may be qualitative. As a non-limiting example, label 136 for the severity of a pulmonary edema may comprise "none," "vascular congestion," interstitial edema," and "alveolar edema." As a nonlimiting example, label 136 may include labels denoting severity such as "mild," "moderate," "severe," and the like. One of ordinary skill in the art, after having reviewed the entirety of this disclosure, would appreciate that a variety of qualitative labels are possible. In some embodiments, label 136 may be a numerical score. For example, label 136 may include a rating of severity of a range of 0-1, 0-3, 0-5, 1-5, 1-10, 1-100, and the like. In some embodiments, a higher rating of severity indicates a higher severity of the medical condition, whereas a lower rating of severity indicates a lower severity of the medical condition. In some embodiments, label 136 may include a percentage. For example, label 136 may use low percentages to indicate low severity and high percentages to indicate high severity.

With continued reference to FIG. 1, label 136 may include a diagnosis. For the purposes of this disclosure a "diagnosis" is an indication of the presence or absence of a medical condition. For example, label 136 may include a diagnosis that a patient has a medical condition or a diagnosis that a patient does not have a medical condition. As a non-limiting example, label 136 may include a diagnosis that a patient does not have pulmonary edema.

With continued reference to FIG. 1, in some embodiments, label 136 may be included in a classifier report 140. Classifier report 140 may include one or more label 136. For example, classifier report 140 may include both label 136 denoting severity of the medical condition, as well as a diagnosis. In some embodiments, processor 104 may be configured to provide a textual explanation of label 136 received from medical image classifier 124. This textual explanation may be included within classifier report 140. For the purposes of this disclosure, a "textual explanation" is a string of text providing additional context to a label. For example, the textual explanation may include an explanation of the reasoning behind label 136. As a non-limiting example, the textual explanation may explain why label 136 contained a diagnosis, diagnosing a patient with a medical condition based on medical image 116. This may include providing specific features of medical image 116 that were most influential in informing the diagnosis. As a further non-limiting example, the textual explanation may include an explanation of the reasoning behind a severity of the medical condition. This may include providing specific features of medical image 116 that were most influential in informing the severity.

Figure 2:
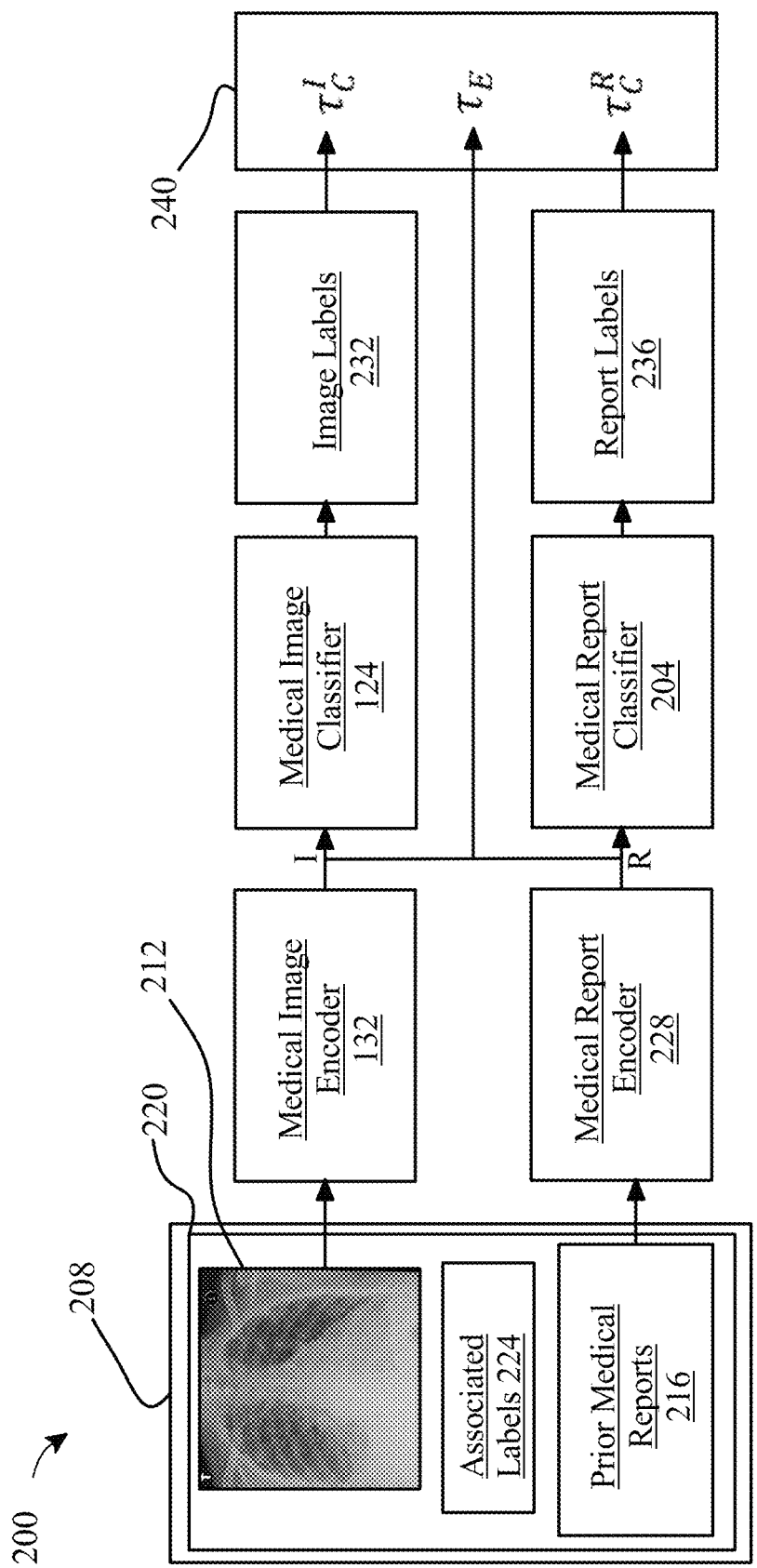
FIG. 2 is a box diagram of an exemplary embodiment of a medical image classifier and medical report classifier training system.

Referring now to FIG. 2, a medical image classifier and medical report classifier training system 200 is illustrated. Processor 104 and/or computing device 112 of FIG. 1 may train a medical image classifier 124 and a medical report classifier 204. Training the medical image classifier 124 and the medical report classifier 204 includes receiving training data 208. "Training data," as used herein, is data containing correlations that a machine-learning process may use to model relationships between two or more categories of data elements. Training data 208 may include a plurality of prior medical images 212 and a plurality of prior medical reports 216. Prior medical images are medical images that are not being used to diagnose a patient or generate a label 136. For example, prior medical images 212 may be medical images from past years, where the subjects of those prior medical images 212 have already received diagnoses, severity labels, and the like. "prior medical reports" are, for the purposes of this disclosure, already existing medical reports. A "medical report," for the purposes of this disclosure, is a report containing a trained professional's interpretation of a medical image. Each prior medical image 212 of the of the plurality of prior medical images 212 is associated with a prior medical report 216 of the plurality of prior medical reports 216 to form an image-text pair 220. For the purposes of this disclosure, a prior medical image 212 is "associated" with a prior medical report 216 when the contents of the prior medical report 216 concerns the prior medical image 212. For example, a prior medical report 216 interpreting a prior medical image 212 would be associated with the prior medical image 212.

With continued reference to FIG. 2, in some embodiments, training data 208 may comprise a plurality of associated labels 224. The plurality of associated labels 224 may be consistent with the label 136 disclosed with reference to FIG. 1. In some embodiments, processor 104 and/or computing device 112 may be configured to receive associated labels. In some embodiments, there may be $N_L$ image-text pairs 220 with associated labels 224. In some embodiments, associated labels 224 may be referred to using Y, wherein the associated labels are represented by $Y=\{y_j\}_{j=1}^{N_L}$. In some embodiments, associated labels 224 may be severity labels as disclosed in this disclosure. As a non-limiting example, associated labels 224 may be edema severity labels. For example, associated labels 224 may be a quantitative representation of edema severity. Thus, associated labels 224 may include severity labels on a numeric scale, such that, as a non-limiting example, y∈{0, 1, 2, 3}.

With continued reference to FIG. 2, in some embodiments, training data 208 may be stored on and retrieved from a training data database. Training data database may be implemented, without limitation, as a relational database, a key-value retrieval database such as a NOSQL database, or any other format or structure for use as a database that a person skilled in the art would recognize as suitable upon review of the entirety of this disclosure. Training data database may alternatively or additionally be implemented using a distributed data storage protocol and/or data structure, such as a distributed hash table or the like. Training data database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 2, training data 208 may comprise a plurality of associated labels 224. For the purposes of this disclosure, an "associated label" is a label that is associated with an image-text pair. Associated labels 224 may be consistent with any labels disclosed in this disclosure. Each associated label 224 may be associated with an image-text pair 220. Associated label 224 may be generated by a trained professional. As a non-limiting example, associated label 224 may be generated by a radiologist. As another non-limiting example, associated label 224 may be generated by a board-certified radiologist. In some embodiments, associated label 224 may be generated by a medical student. As a non-limiting example, associated label 224 may be generated by a resident. In some embodiments, associated labels 224 may be stored in training data database. One of ordinary skill in the art, after having reviewed the entirety of this disclosure, would appreciate that associated labels 224 may be generated by anyone having the relevant training and experience in the field to which the associated prior medical images 212 and/or prior medical reports 216 pertain.

With continued reference to FIG. 2, training data 208 may include prior image labels. Prior image labels may be consistent with any image labels disclosed as part of this disclosure (particularly image labels 232), except that they pertain to prior medical image 212. Prior image labels may be associated with a prior medical image 212 of the plurality of prior medical images 212. Prior image labels may be received from training data database. In some embodiments, prior image labels may be manually generated. As a non-limiting example, prior image labels may be generated by a radiologist. As another non-limiting example, prior image labels may be generated by a board-certified radiologist. As another non-limiting example, prior image labels may be generated by a medical student. As another non-limiting example, prior image labels may be generated by a resident. In an embodiment, prior image labels, and/or training data 208 may be obtained and/or generated from one or more sources including but not limited to journal articles, publications, research papers, open source and the like. One of ordinary skill in the art, after having reviewed the entirety of this disclosure, would appreciate that the prior image labels may be generated by anyone having the relevant training and experience in the field to which the associated prior medical images 212 pertain.

With continued reference to FIG. 2, prior medical report 216 may contain diagnosis regarding the presence or absence of a medical condition, the severity of a medical condition, the needed treatment speed for the medical condition, and the like.

With continued reference to FIG. 2, prior medical report 216 may include a radiology report. A "radiology report," for the purposes of this disclosure is a medical report concerning a medical image generated using radiography. The radiology report may contain a trained professional's interpretation of a radiograph. In some embodiments, the radiology report may contain a trained professional's interpretation of a chest radiograph. As a non-limiting example, the radiology report may include an interpretation regarding the presence or absence of a pulmonary edema. As a non-limiting example, the radiology report may include an interpretation regarding the severity of a pulmonary edema.

With continued reference to FIG. 2, training data 208 may be augmented. In some embodiments, prior medical images 212 may be augmented by translating and rotating them. This may be performed on the fly during training. The size of medical images, such as chest radiographs varies and is approximately 3000×3000 pixels. Thus, the size of the medical images may be cropped to a uniform size as part of data augmentation. As a non-limiting example, prior medical images 212 may be cropped to 2048×2048 pixels.

With continued reference to FIG. 2, system 200 may include a training medical report encoder 228. A "medical report encoder," for the purposes of this disclosure, is an element that converts text into text features. Training medical report encoder 228 may be a Bidirectional Encoder Representations from Transformers (BERT) model. A BERT model is a machine learning technique for natural language processing. In some embodiments, the BERT model may use the beginner classification ([CLS]) token's hidden unit size of 768 and maximum sequence length of 320. The BERT model's parameters may be initialized using pre-trained weights on scientific text. The text features may be represented as 768-dimensional vectors in the joint embedding space.

With continued reference to FIG. 2, training medical report encoder 228 may tokenize the text of a received prior medical report 216. For the purposes of this disclosure, "tokenization" refers to splitting a phrase, sentence, paragraph, or entire text of a document into smaller units, such as individual words or terms. These smaller units may be referred to as "tokens." In some embodiments, tokenizing prior medical report 216 may include splitting prior medical report 216 into tokens, Tokenization, as non-limiting examples, may take the form of word tokenization, character tokenization, n-gram tokenization, and/or sub-word tokenization. Word tokenization may, for example, split a sentence up into tokens based on the location of spaces, such that each word in the sentence is a token. Character tokenization may, for example, split a sentence up into tokens such that each character in the sentence is a token. N-gram tokenization may, for example, split a sentence up into tokens of length "n" characters. Subword tokenization may, for example, split a word into sub-words, wherein the sub-words are tokens. As a non-limiting example, "returning" may be split into tokens of "re," "turn," and "ing." In some embodiments, training medical report encoder 228 may perform tokenization using ScispaSci. ScispaSci is a Python package containing spaCy models for processing biomedical, scientific, or clinical text. In some embodiments, a BERT tokenizer may be used to perform tokenization.

With continued reference to FIG. 2, in some embodiments, medical report encoder 228 may include a language processing module. Language processing module may include any hardware and/or software module. Language processing module may be configured to extract, from the one or more documents, one or more words. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 2, language processing module may operate to produce a language processing model. Language processing model may include a program automatically generated by computing device and/or language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

Still referring to FIG. 2, language processing module and/or diagnostic engine may generate the language processing model by any suitable method, including without limitation a natural language processing classification algorithm; language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 2, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 2, language processing module may use a corpus of documents to generate associations between language elements in a language processing module, and diagnostic engine may then use such associations to analyze words extracted from one or more documents and determine that the one or more documents indicate significance of a category. In an embodiment, language module and/or processor 104 may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into processor 104. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York.

With continued reference to FIG. 2 in some embodiments, system 200 may use optical character recognition. In some embodiments, medical report encoder 228 may apply optical character recognition to prior medical report 216. In some embodiments, optical character recognition or optical character reader (OCR) includes automatic conversion of images of written (e.g., typed, handwritten or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 2, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 2, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases. a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

Still referring to FIG. 2, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

Still referring to FIG. 2, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 3-7. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 2, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIGS. 3-7.

Still referring to FIG. 2, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make use of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

With continued reference to FIG. 2, certain sections of prior medical reports 216 may be extracted to be used for training in system 200. As a non-limiting example, the sections of "impressions," "findings," "conclusion," and/or "recommendation may be extracted. In some embodiments, particularly when none of the aforementioned sections are present, the "final report" section may be extracted.

With continued reference to FIG. 2, system 200 may include an medical image encoder 132 as disclosed with reference to FIG. 1. In some embodiments, medical image encoder 132 may be implemented as a series of residual blocks. The medical image encoder 132 may be trained using a random initialization. In some embodiments, medical image encoder 132 may encode medical image 116. In some embodiments, encoding medical image 116 may include extracting image features. In some embodiments, medical image encoder 132 may encode prior medical image 212. In some embodiments, encoding prior medical image 212 may include extracting image features.

With continued reference to FIG. 2, in some embodiments, medical image encoder 132 and/or training medical report encoder 228 be trained using a ranking-based criterion. In some embodiments, ranking-based criterion may be used to train medical image encoder 132 and training medical report encoder 228 parameterized by $\theta_E^I$ and $\theta_E^R$ respectively to learn image and text feature representations $I(x^I;\theta_E^I)$ and $R(x^R;\theta_E^R)$. As a non-limiting example, when given an image-text pair 220 $(x_j^I, x_j^R)$, an imposter image $(x_{s(j)}^I)$ and an imposter report $(x_{s(j)}^R)$ may be randomly selected from training data 208 (X). The random selection may be conducted using a map function s(j) that produces a random permutation of {0, 1, 2, 3 ..., N}. This imposter selection may be conducted at the beginning of each training epoch. A "training epoch," for the purposes of this disclosure, is a period denoting training using all of the training data once.

With continued reference to FIG. 2, medical image encoder 132 may receive medical images 116. Medical image encoder 132 may output image embeddings (I). Training medical report encoder 228 may receive prior medical reports 216. Training medical report encoder 228 may output text embeddings (R). For the purposes of this disclosure, an "image embedding" is a lower dimensional representation of an image. In some embodiments, an image embedding may be a dense vector representation of an image. For the purposes of this disclosure, a "text embedding," is a vector representation of text.

With continued reference to FIG. 2, in some embodiments, system 200 may construct a joint image-text embedding space using medical image encoder 132 and training medical report encoder 228 to extract image features and text features respectively.

With continued reference to FIG. 2, in some embodiments, in applying a ranking-based criterion, feature representations between a matched pair of image embedding and text embedding $(I_j, R_j)$ may be encouraged to be closer than mismatched pairs. For example, the mismatched pairs generated by the imposter selection disclosed above, i.e. $(I_{s(j)}, R_j)$ and $(I_j, R_{s(j)})$. While the distance between I and R could be directly minimized, this may push the image and text features into a small cluster in the embedding space. Another option is to construct a loss function that spreads out feature representation in the embedding space. This may help with downstream classification. In some embodiments, the loss function for the encoders $(\tau_E)$, including medical image encoder 132 and training medical report encoder 228, may be:

$$\tau_E(\theta_E^I,\theta_E^R;x_j,x_{s(j)})=\max(0,\text{Sim}(I_j,R_{s(j)})-\text{Sim}(I_j,R_j)+\eta)+\max(0,\text{Sim}(I_{s(j)},R_j)-\text{Sim}(I_j,R_j)+\eta)$$

Sim(•,•) is the similarity measurement of two feature representations in the joint embedding space. η is a margin parameter. The similarity measurement may use the dot product. In some embodiments, where both $j \leq N_L$ and $s(j) \leq N_L$, wherein $N_L$ is the number of image-text pairs 220 with an associated label 224, η may be set to $|y_j - y_{s(j)}|$. Otherwise, η may be set equal to 0.5. The margin parameter may be determined by the difference due to the mismatch between $y_j$ and $y_{s(j)}$, if both labels (associated labels 224) are known. Otherwise, the margin parameter may be set equal to a constant.

With continued reference to FIG. 2, medical image classifier 124 and medical report classifier 204 are trained by processor 104 and/or computing device 112. In some embodiments, machine learning module 128 may be used to train medical image classifier 124 and/or medical report classifier 204. Training medical image classifier 124 and medical report classifier 204 includes receiving training data 208. Medical image classifier 124 may have four residual blocks followed by two fully connected convolutional layers. Processor 104 and/or computing device 112 are configured to train medical image classifier 124 and medical report classifier 204 using training data 208.

With continued reference to FIG. 2, processor 104 may train a classifier, such as medical image classifier 124 and/or medical report classifier 204 using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, processor 104 may train a classifier, such as medical image classifier 124 and/or medical report classifier 204 using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in a database, and classifying the known sample; this may be performed recursively and/or iteratively to generate classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 2, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l = \sqrt{\sum_{i=0}^{n} a_i^2}$, where ai is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With continued reference to FIG. 2, medical image classifier 124 may output image labels 232. Image labels 232 may be consistent with labels 136 disclosed as part of this disclosure with reference to FIG. 1. Image labels 232 may be expressed as $\hat{y}^I(I; \theta_C^I)$. Medical report classifier 204 may output report labels 236. Report labels 236 may be consistent with any labels disclosed as part of this disclosure. Report labels 236 may be expressed as $\hat{y}^R(R; \theta_C^R)$.

With continued reference to FIG. 2, medical image classifier 124 and/or medical report classifier 204 may be optimized using a loss function. A "loss function," for the purposes of this disclosure is a function that uses on or more variables in order to evaluate the accuracy of an algorithm. A loss function may measure how for an estimated value is from its true value. This distance may be referred to as "loss" or "cost." In optimization problems, a loss function may be sought to be minimized. For example, processor 104 may optimize a classifier, such as medical image classifier 124 and/or medical report classifier 204, by minimizing a loss function.

With continued reference to FIG. 2, training the medical image classifier 124 and medical report classifier 204 includes optimizing medical image classifier 124 using a common loss function 240 comprising output of medical image classifier 124 and medical report classifier 204. In some embodiments, optimizing medical image classifier 124 may include optimizing both of medical image classifier 124 and medical report classifier 204 using common loss function 240. The output of medical image classifier 124 and medical report classifier 204 may include image labels 232 and report labels 236, respectively. The problem of classification for the medical reports and medical images may be treated as a multi-class classification. That is, the outputs of the classifiers ($\hat{y}^I$ and $\hat{y}^R$) are encoded as one-hot 4-dimensional vectors. Cross-entropy may be used to construct a loss function for the classifiers. A loss function for medical image classifier 124 may be:

$$\tau_C^I(\theta_E^I, \theta_C^I, x_j, y_j) = -\sum_{i=0}^{3} y_{ji} \log \hat{y}_i^I(I_j(x_j^I; \theta_E^I); \theta_C^I)$$

With continued reference to FIG. 2, a loss function for medical report classifier 204 may be:

$$\tau_C^R(\theta_E^R, \theta_C^R, x_j, y_j) = -\sum_{i=0}^{3} y_{ji} \log \hat{y}_i^R(R_j(x_j^R; \theta_E^R); \theta_C^R)$$

With continued reference to FIG. 2, these loss functions for medical image classifier 124 ($\tau_C^I$) and report classifier ($\tau_C^R$) may be combined to form a joint loss function for the classifiers:

$$\tau_c(\theta_E^I, \theta_C^I, \theta_E^R, \theta_C^R, x_j, y_j) = \tau_C^I(\theta_E^I, \theta_C^I, x_j, y_j) + \tau_C^R(\theta_E^R, \theta_C^R, x_j, y_j)$$

With continued reference to FIG. 2, common loss function 240 may be constructed using loss functions for $\tau_E$, $\tau_C^I$, and $\tau_C^R$. Thus, common loss function 240 may be expressed as:

$$\tau(\theta_E^I, \theta_C^I, \theta_E^R, \theta_C^R; X, Y) = \sum_{j=1}^{N} \tau_E(\theta_E^I, \theta_E^R; x_j, x_{s(j)}) + \sum_{j=1}^{N_L} \tau_C(\theta_E^I, \theta_C^I, \theta_E^R, \theta_C^R; x_j, y_j)$$

With continued reference to FIG. 2, processor 104 and/or computing device 112 may optimize medical image classifier 124 and medical report classifier 204 using common loss function 240. In some embodiments, a stochastic gradient-based optimization procedure may be used to minimize the loss in common loss function 240. As a non-limiting example, stochastic gradient-based optimization procedure AdamW may be used to minimize the loss in common loss function 240. In some embodiments, a warm-up linear scheduler may be used for the learning rate. The model created by system 200 may be trained on all image-text pairs by optimizing the first term in the common loss function 240 reproduced above for 10 epochs. In some embodiments, the model may then be trained on labeled image-text pairs by optimizing common loss function 240 for 50 epochs. The mini-batch size may be 4.

With continued reference to FIG. 2, medical image classifier 124 and medical report classifier 204 may be trained to classify image labels 232 and report labels 236, respectively, independently from the image features and from the text features. Using this arrangement, medical image classifier 124 may be decoupled from medical report classifier Thus, processor 104 and/or computing device 112 may be configured to decouple medical image classifier 124 from medical report classifier 204 after training medical image classifier 124 and medical report classifier 204. Image classification and text classification may be decoupled at inference time (e.g. when medical image classifier 124 generates label 136 in FIG. 1).

Figure 3:
FIG. 3 is a diagram of an exemplary embodiment of an architecture for an image encoder and classifier.

Referring now to FIG. 3, an exemplary embodiment of architecture 300 for an image encoder and classifier is shown. Image encoder may be consistent with medical image encoder 132. image classifier may be consistent with medical image classifier 124. Each residual block in FIG. 3 may have 3 convolutional layers.

Figure 4:
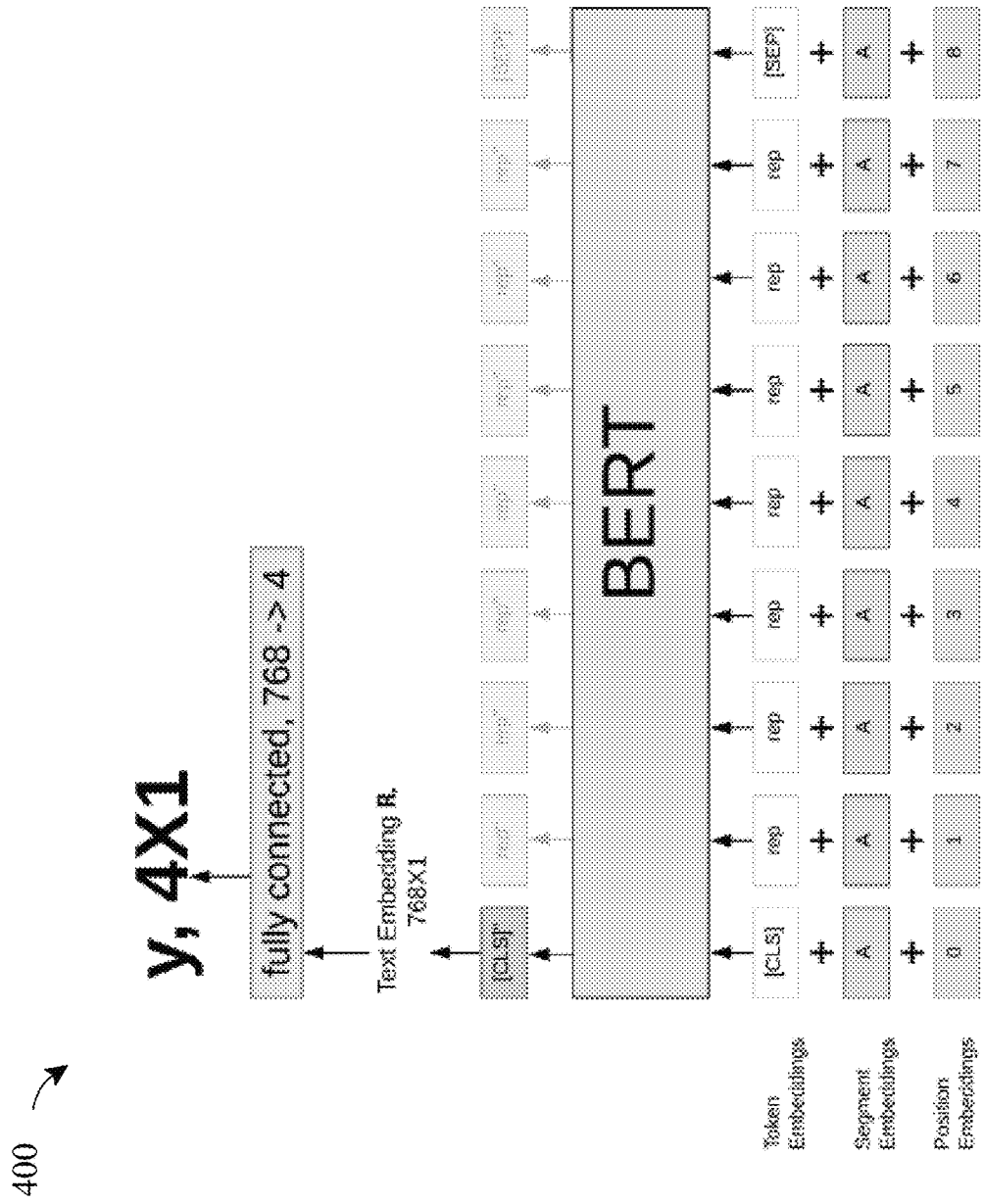
FIG. 4 is a diagram of an exemplary embodiment of an architecture for a text encoder and classifier.

Referring now to FIG. 4, an exemplary embodiment of architecture 400 for a text encoder and classifier is shown. Text encoder may be consistent with training medical report encoder 228. Text classifier may be consistent with medical report classifier 204. Architecture 400 may use the BERT model. A full medical report, such as a radiology report may be encoded between the [CLS] and [SEP] tokens in FIG. 4. "Rep," as seen in FIG. 4, represents the text associated with a medical report. The maximum input sequence length for the text encoder may be set to 320.

Figure 5:
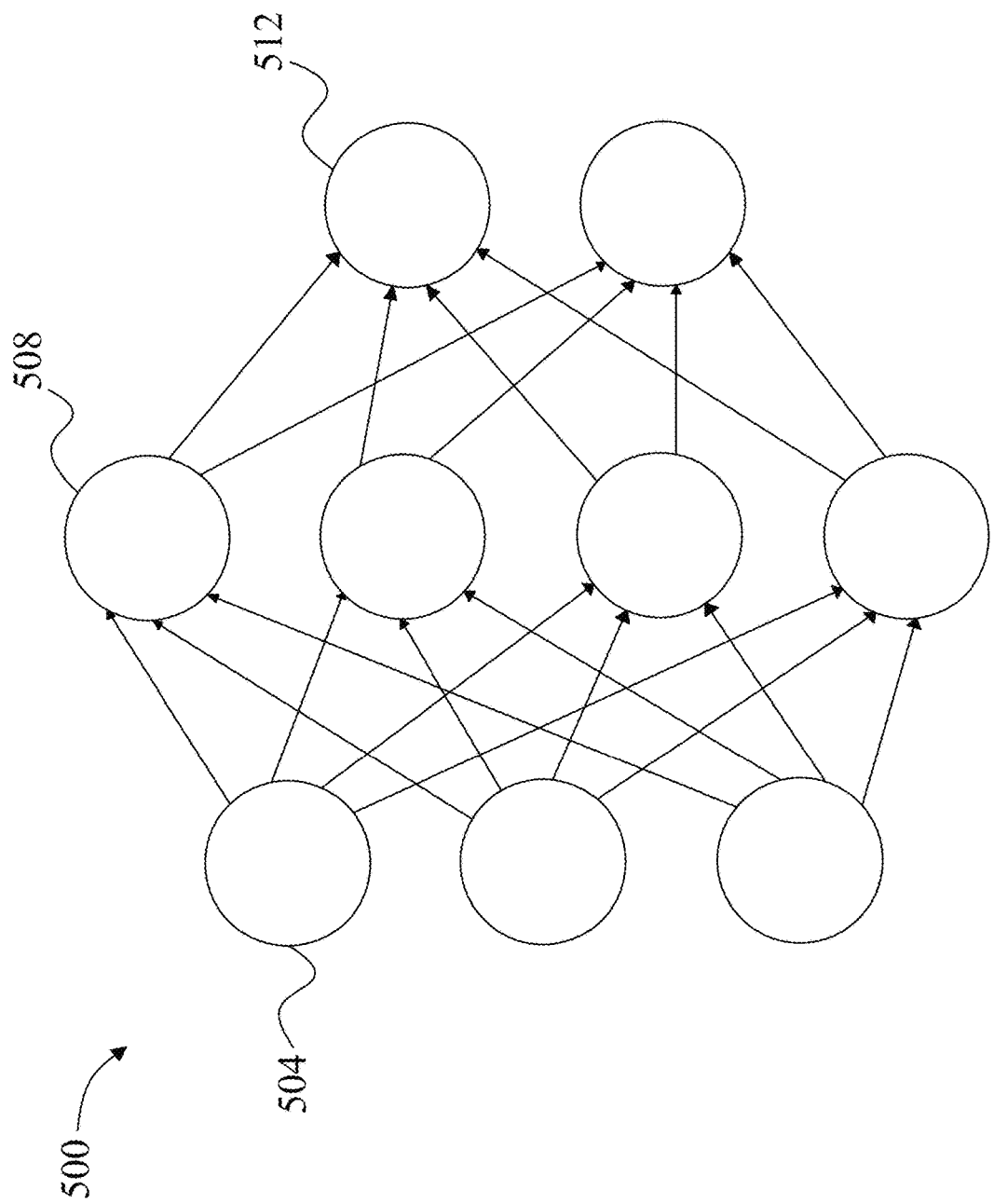
FIG. 5 is a diagram of an exemplary embodiment of neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 6:
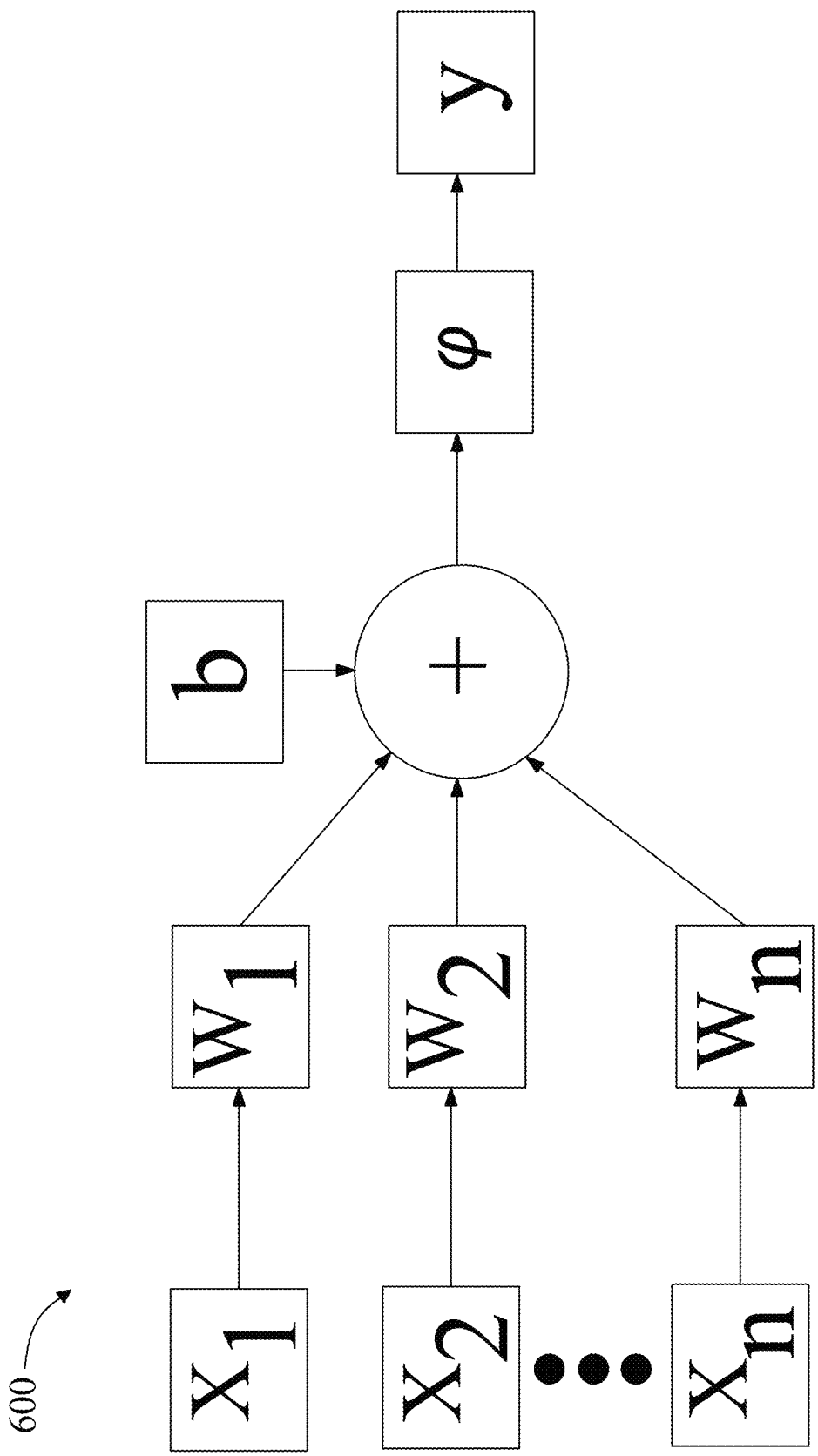
FIG. 6 is a diagram of an exemplary embodiment of a node of a neural network.

Referring now to FIG. 6, an exemplary embodiment of a node 600 of a neural network is illustrated. A node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x^i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 7:
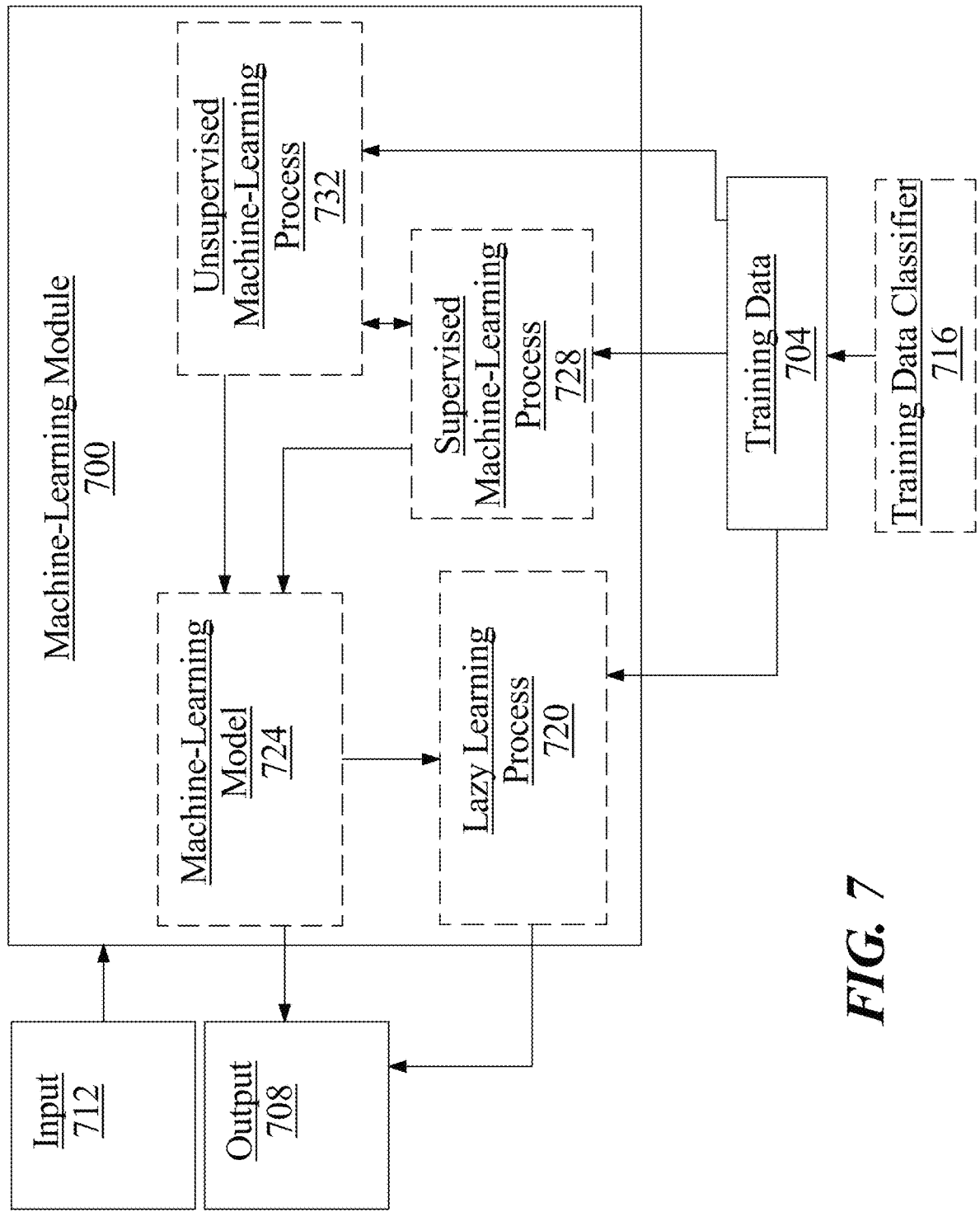
FIG. 7 is a box diagram of an exemplary embodiment of a machine learning module.

Referring now to FIG. 7, an exemplary embodiment of a machine-learning module 700 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 704 to generate an algorithm that will be performed by a computing device/module to produce outputs 708 given data provided as inputs 712; this is in contrast to a non-machine learning software program where the commands to be executed are determined in advance by a user and written in a programming language.

Still referring to FIG. 7, Training data 704 may include a plurality of data entries, each entry representing a set of data elements that were recorded, received, and/or generated together; data elements may be correlated by shared existence in a given data entry, by proximity in a given data entry, or the like. Multiple data entries in training data 704 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 704 according to various correlations; correlations may indicate causative and/or predictive links between categories of data elements, which may be modeled as relationships such as mathematical relationships by machine-learning processes as described in further detail below. Training data 704 may be formatted and/or organized by categories of data elements, for instance by associating data elements with one or more descriptors corresponding to categories of data elements. As a non-limiting example, training data 704 may include data entered in standardized forms by persons or processes, such that entry of a given data element in a given field in a form may be mapped to one or more descriptors of categories. Elements in training data 704 may be linked to descriptors of categories by tags, tokens, or other data elements; for instance, and without limitation, training data 704 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 7, training data 704 may include one or more elements that are not categorized; that is, training data 704 may not be formatted or contain descriptors for some elements of data. Machine-learning algorithms and/or other processes may sort training data 704 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatically may enable the same training data 704 to be made applicable for two or more distinct machine-learning algorithms as described in further detail below. Training data 704 used by machine-learning module 700 may correlate any input data as described in this disclosure to any output data as described in this disclosure. As a non-limiting illustrative, inputs and outputs to be described later.

Further referring to FIG. 7, training data may be filtered, sorted, and/or selected using one or more supervised and/or unsupervised machine-learning processes and/or models as described in further detail below; such models may include without limitation a training data classifier 716. Training data classifier 716 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 700 may generate a classifier using a classification algorithm, defined as a processes whereby a computing device and/or any module and/or component operating thereon derives a classifier from training data 704. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 716 may classify elements of training data to severity labels, diagnoses, medical treatment plans, and the like.

Still referring to FIG. 7, machine-learning module 700 may be configured to perform a lazy-learning process 720 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 704. Heuristic may include selecting some number of highest-ranking associations and/or training data 704 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 7, machine-learning processes as described in this disclosure may be used to generate machine-learning models 724. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 724 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 724 may be generated by creating an artificial neural network, such as a convolutional neural network comprising an input layer of nodes, one or more intermediate layers, and an output layer of nodes. Connections between nodes may be created via the process of "training" the network, in which elements from a training data 704 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 7, machine-learning algorithms may include at least a supervised machine-learning process 728. At least a supervised machine-learning process 728, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include prior medical images 212 or prior medical reports 216 as described above as inputs, labels 136, severity labels, classifier reports 140, and diagnoses as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 704. Persons skilled in the art, upon reviewing the entirety of this disclosure, will be aware of various possible variations of at least a supervised machine-learning process 728 that may be used to determine relation between inputs and outputs. Supervised machine-learning processes may include classification algorithms as defined above.

Further referring to FIG. 7, machine learning processes may include at least an unsupervised machine-learning processes 732. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 7, machine-learning module 700 may be designed and configured to create a machine-learning model 724 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 7, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 8:
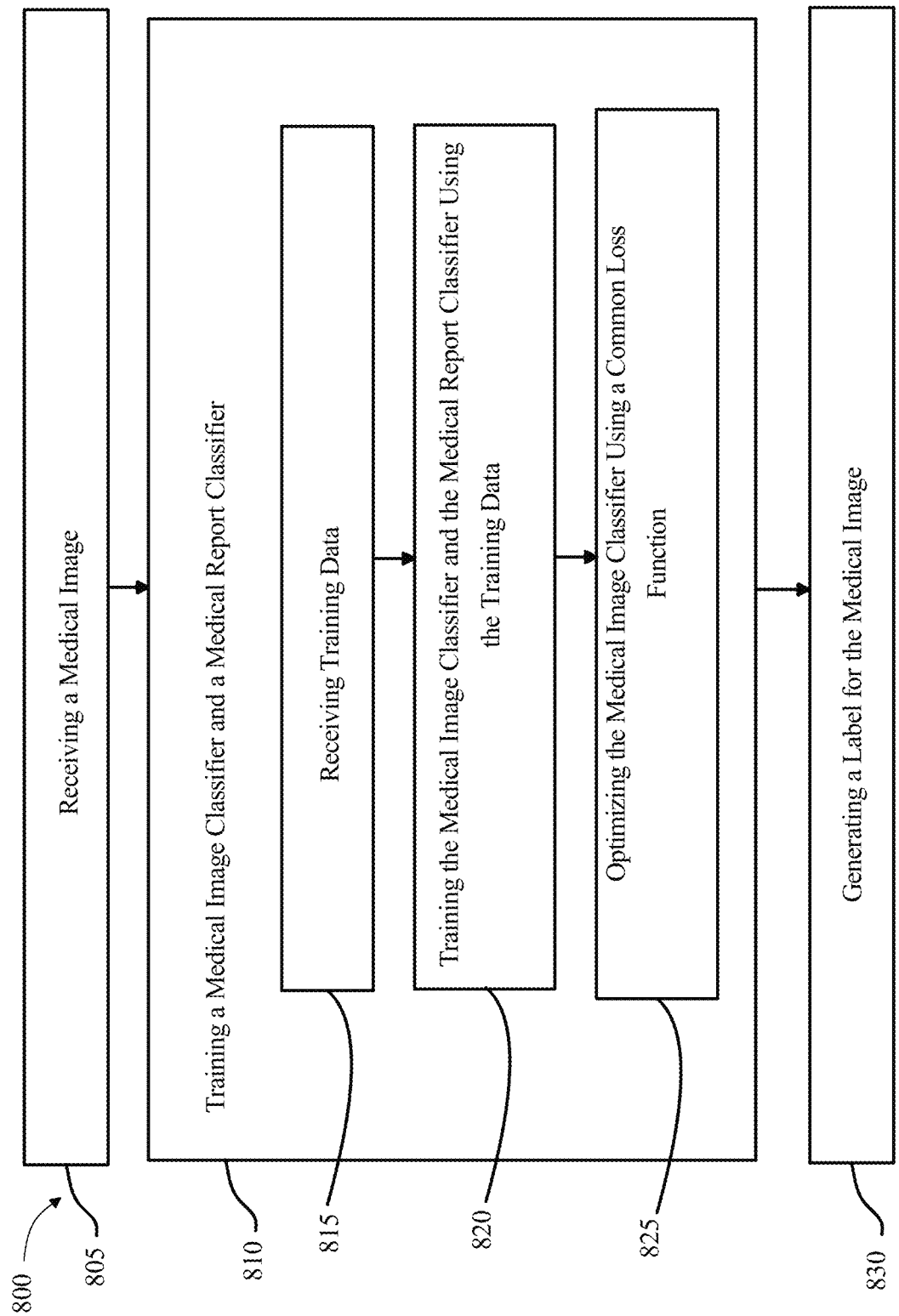
FIG. 8 is a flow diagram of an exemplary embodiment of a method for diagnosing a medical condition is shown.

Referring now to FIG. 8, an exemplary embodiment of a method 800 for diagnosing a medical condition is shown. Method 800 includes a step 805 of receiving a medical image. The medical image is the result of a medical imaging procedure. The medical image may include a chest radiograph. This may be implemented, without limitation, as described above in reference to FIGS. 1-7.

With continued reference to FIG. 8, method 800 includes a step 810 of training a medical image classifier and a medical report classifier. This may be implemented, without limitation, as described above in reference to FIGS. 1-7. Step 810 includes a sub-step 815 of receiving training data. The training data includes a plurality of prior medical images and a plurality of prior medical reports. Each prior medical image of the plurality of prior medical images is associated with a prior medical report of the plurality of prior medical reports to form an image-text pair. In some embodiments, the training data may further include a plurality of associated labels, wherein each associated label is associated with an image text pair. The prior medical report may be a radiology report. This may be implemented, without limitation, as described above in reference to FIGS. 1-7. Step 810 includes a sub-step 820 of training the medical image classifier and the medical report classifier using the training data. This may be implemented, without limitation, as described above in reference to FIGS. 1-7. Step 810 includes a sub-step 825 of optimizing the medical image classifier using a common loss function comprising output of the medical image classifier and the medical report classifier. This may be implemented, without limitation, as described above in reference to FIGS. 1-7. In some embodiments, optimizing the medical image classifier using a common loss function may comprise optimizing both of the image classifier and the medical report classifier using a common loss function. This may be implemented, without limitation, as described above in reference to FIGS. 1-7.

With continued reference to FIG. 8, method 800 includes a step 830 of generating a label for the medical image. Step 830 includes inputting the medical image into the medical image classifier. Step 830 also includes receiving the label as output from the medical image classifier. Label may include a severity of a medical condition. In some embodiments, the label for the medical image may be a severity label, wherein the severity label denotes the severity of a pulmonary edema. This may be implemented, without limitation, as described above in reference to FIGS. 1-7.

With continued reference to FIG. 8, in some embodiments, method 800 may include encoding the medical image, wherein encoding the medical image comprises extracting image features. This may be implemented, without limitation, as described above in reference to FIGS. 1-7. In some embodiments, method 800 may include encoding the prior medical report, wherein encoding the prior medical report comprises extracting text features. In some embodiments, encoding the prior medical report may include tokenizing the prior medical report. Tokenizing the prior medical report may include splitting the medical report into tokens. This may be implemented, without limitation, as described above in reference to FIGS. 1-7.

With continued reference to FIG. 8, in some embodiments, method 800 may include decoupling the medical image classifier from the medical report classifier after training the medical image classifier and the medical report classifier. This may be implemented, without limitation, as described above in reference to FIGS. 1-7. In some embodiments, method 800 may include providing a textual explanation of the label received from the medical image classifier. This may be implemented, without limitation, as described above in reference to FIGS. 1-7.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
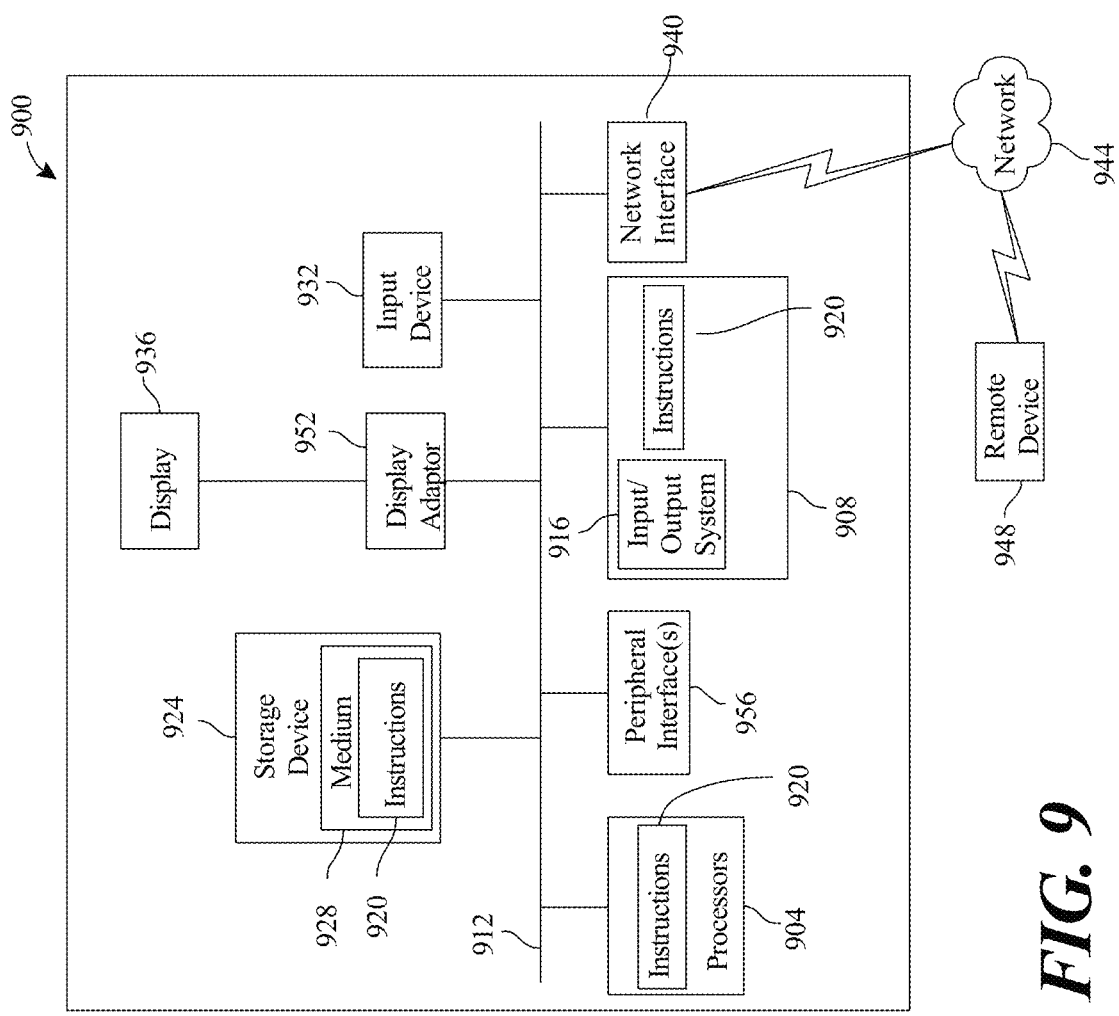
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method for diagnosing a medical condition, the method comprising:
   receiving a medical image selected from the group consisting of radiographs, magnetic resonance imaging, nuclear medicine imaging, or ultrasounds, wherein the medical image is the result of a medical imaging procedure;
   training a medical image encoder, a medical report encoder, and a classifier, wherein training the encoders and classifier comprises:
      receiving training data, wherein the training data comprises a plurality of prior medical images and a plurality of prior medical reports, wherein each prior medical image of the plurality of prior medical images is associated with a prior medical report of the plurality of prior medical reports to form a pair of image-text embeddings, which extract bidirectional encoder representations using neural networks;
      training the medical image encoder and the medical report encoder using the training data; and
      optimizing the encoders using a ranking-based loss function of output embeddings of the medical image encoder and the medical report encoder; and
   generating a label for the medical image, wherein generating the label for the medical image comprises:
      inputting the medical image into the medical image encoder; and
      receiving the label as output from the medical image encoder and the classifier.

2. The method of claim 1, further comprising encoding the medical image, wherein encoding the medical image comprises extracting image features.

3. The method of claim 1, further comprising encoding the prior medical report, wherein encoding the prior medical report comprises extracting text features.

4. The method of claim 3, further comprising tokenizing the prior medical report, wherein tokenizing the prior medical report comprises splitting the medical report into words or letters and converting the words or letters to tokens.

5. The method of claim 1, further comprising, decoupling the medical image encoder from the medical report encoder after training the medical image encoder and the medical report encoder.

6. The method of claim 1, wherein the label comprises a severity of a medical condition.

7. The method of claim 1, wherein the training data further comprises a plurality of associated labels, wherein each associated label is associated with an image-text pair.

8. The method of claim 1, wherein:
   the medical image is a chest radiograph; and
   the prior medical report is a radiology report.

9. The method of claim 8, wherein the label for the medical image is a severity label, wherein the severity label denotes the severity of a pulmonary edema.

10. The method of claim 1, further comprising providing a textual explanation of the label received from the medical image classifier.

11. An apparatus for diagnosing a medical condition, the apparatus comprising:
    at least a processor; and
    a memory communicatively connected to the processor, the memory containing instructions configuring the at least a processor to:
       receive a medical image selected from the group consisting of radiographs, magnetic resonance imaging, nuclear medicine imaging, or ultrasounds, and is, wherein the medical image is the result of a medical imaging procedure;
       train a medical image encoder and a medical report encoder, wherein training the medical image encoder and the medical report encoder comprises:
          receiving training data, wherein the training data comprises a plurality of prior medical images and a plurality of prior medical reports, wherein each prior medical image of the plurality of prior medical images is associated with a prior medical report of the plurality of prior medical reports to form a pair of image-text embeddings, which extract bidirectional encoder representations using neural networks;
          training the medical image encoder and the medical report encoder using the training data; and
          optimizing the encoders using a ranking-based loss function of output embeddings of the medical image encoder and the medical report encoder; and
       generate a label for the medical image, wherein generating the label for the medical image comprises:
          inputting the medical image into the medical image classifier; and
          receiving the label as output from the medical image classifier.

12. The apparatus of claim 11, wherein the memory contains instructions further configuring the processor to encode the medical image, wherein encoding the medical image comprises extracting image features.

13. The apparatus of claim 11, wherein the memory contains instructions further configuring the processor to encode the prior medical report, wherein encoding the prior medical report comprises extracting text features.

14. The apparatus of claim 13, wherein the memory contains instructions further configuring the processor to tokenize the prior medical report, wherein tokenizing the prior medical report comprises splitting the medical report into words or letters and converting the words or letters to tokens.

15. The apparatus of claim 11, wherein the memory contains instructions further configuring the processor to decouple the medical image encoder from the medical report encoder after training the medical image encoder and the medical report encoder.

16. The apparatus of claim 11, wherein the label comprises a severity of a medical condition.

17. The apparatus of claim 11, wherein the training data further comprises a plurality of associated labels, wherein each associated label is associated with an image-text pair.

18. The apparatus of claim 11, wherein:
    the medical image is a chest radiograph; and
    the prior medical report is a radiology report.

19. The apparatus of claim 18, wherein the label for the medical image is a severity label, wherein the severity label denotes the severity of a pulmonary edema.

20. The apparatus of claim 11, wherein the memory contains instructions further configuring the processor to provide a textual explanation of the label received from the medical image classifier.

* * * * *